United States Patent
De Angelis

(10) Patent No.: US 6,927,066 B1
(45) Date of Patent: Aug. 9, 2005

(54) PROCESS FOR THE DETERMINATION OF MTBE IN THE GROUND AND AIR

(75) Inventor: Lucio De Angelis, Rome (IT)

(73) Assignee: Enitecnologie S.p.A., San Donato Milanese (IT)

( * ) Notice: Subject to any disclaimer, the term of this patent is extended or adjusted under 35 U.S.C. 154(b) by 0 days.

(21) Appl. No.: 09/581,264

(22) PCT Filed: Feb. 18, 1999

(86) PCT No.: PCT/EP99/01821

§ 371 (c)(1),
(2), (4) Date: Jun. 28, 2000

(87) PCT Pub. No.: WO99/63340

PCT Pub. Date: Dec. 9, 1999

(30) Foreign Application Priority Data

Jun. 4, 1998 (IT) .......................................... MI98A1248

(51) Int. Cl.⁷ .............................................. G01N 33/24
(52) U.S. Cl. ......................... 436/128; 436/127; 436/25; 436/807; 422/57; 422/58; 422/83; 422/98; 73/23.2

(58) Field of Search ................................. 436/128, 127, 436/25, 807; 422/57, 58, 83, 98; 73/23.2

(56) References Cited

U.S. PATENT DOCUMENTS

| 5,400,643 A | * | 3/1995 | De Angelis et al. | ......... 340/634 |
| 5,447,054 A | * | 9/1995 | Modica et al. | ............. 73/31.06 |
| 5,573,728 A | * | 11/1996 | Loesch et al. | ................ 422/90 |
| 5,811,662 A | * | 9/1998 | Williams et al. | ............ 585/617 |

\* cited by examiner

*Primary Examiner*—Jill Warden
*Assistant Examiner*—LaToya I. Cross
(74) *Attorney, Agent, or Firm*—Oblon, Spivak, McClelland, Maier & Neustadt, P.C.

(57) ABSTRACT

A process is described, and also the system for its embodiment, for the determination of pollution by MTBE in the soil and in the overlying atmosphere. An example is described relating to the monitoring of underground fuel tanks for autotraction containing an oxygenated additive.

3 Claims, 4 Drawing Sheets

PROCESS FOR THE DETERMINATION OF MTBE IN THE GROUND AND AIR

The present invention relates to a process for the determination of pollution by methyl ter butyl ether.

Methyl ter butyl ether (MTBE) is the most widely used among oxygenated additives for motor vehicles. Its addition improves combustion and significantly reduces the emission of carbon monoxide, especially during low winter temperatures. The possibility of a leakage in the earth of fuels contained in underground tanks of service stations is probable. As a result of this, MTBE has been the object of a great deal of research with respect to its destiny in the environment and its potential impact on public health, mainly bearing in mind that this substance is extremely volatile and soluble in water. In addition, if present, it remains in deep water and sediments as owing to its very limited biodegradability, with an odour that can be noticed starting from concentrations at a level of 20 ppb. Its cancerogenous activity, if existing, seems to be small.

There are various methods for determining and measuring MTBE: they range from gas chromatography to IRA and flame-ionization, but they are all difficult to apply to the ground.

We have now overcome these problems by means of a process which allows the continuous monitoring of MTBE, in the ground and on the surface, using sensors in the solid state.

In accordance with this, the present invention relates to a process for monitoring methyl ter butyl ether (MTBE) vapours, in concentrations equal to or higher than 0.1 ppm, in the ground and overlying atmosphere comprising:

a) adopting a series of MTBE vapour sensors of which at least one in the earth, equipped with a membrane permeable to gases and impermeable to water, and at least one in the air on the surface of the ground, these sensors consisting of a sensitive element made of a semi-conductor metal oxide containing platinum;

a heater capable of bringing the temperature of said sensitive element to a range of 300 and 500° C.;

b) continuously observing the resistance variations of the sensitive elements by interaction with MTBE, comparing the signals emitted by the sensor in the earth and the sensor in the air on the ground-surface;

evaluating on the basis of this comparison the presence and concentration of MTBE in the surface layers or depths of the ground and in the atmosphere above the ground itself.

A further object of the present invention relates to the device for effecting the process.

A typical embodiment of the invention is described hereunder, with reference to FIGS. 1 and 2 in which equal numbers correspond to equal elements.

BRIEF DESCRIPTION OF THE DRAWINGS

FIG. 1 illustrates a sensor, in enlarged form. The sensitive element 1 is produced by placing by screen printing, on an aluminum slab with dimensions of 3×9×0.25 mm, a 40 micron layer of a tin oxide paste, containing platinum. Powders are used having a particle size of less than 1 micron containing from 20 to 30% by weight of alumina and organometallic platinum as catalyst in a quantity ranging from 0.1 to 1% by weight. A resistor (consisting of a layer of any commercial screen printing conductor paste capable of resisting at least 400° C.) is deposited, again by screen printing, on the opposite side of the slab, to keep the sensitive element at an operating temperature of 300–500° C. After depositing the electric contacts also by screen printing, the slab is subjected to a baking step in an oven at 800–1000° C. for an hour.

Finally the device, which forms the sensitive element, is assembled on a TO78 2 container and inserted in a steel cylinder 3 closed by means of a flame-shield net 4. If the sensor described is fixed into the ground, a membrane 5, permeable to gases and impermeable to water, is inserted under the flame-shield net to prevent any possible water present in the earth from entering into contact with the sensitive element. An appropriate porous septum or even better a membrane made of ePFTE material can be used for the purpose.

The sensitive elements can alternatively be produced with other types of semi-conductor metal oxides, but still using platinum as catalyst.

The sensors are equipped with feeders, or alternatively batteries, to supply energy to the heater and resistivity measurement circuit of the sensitive element.

Figure 1:
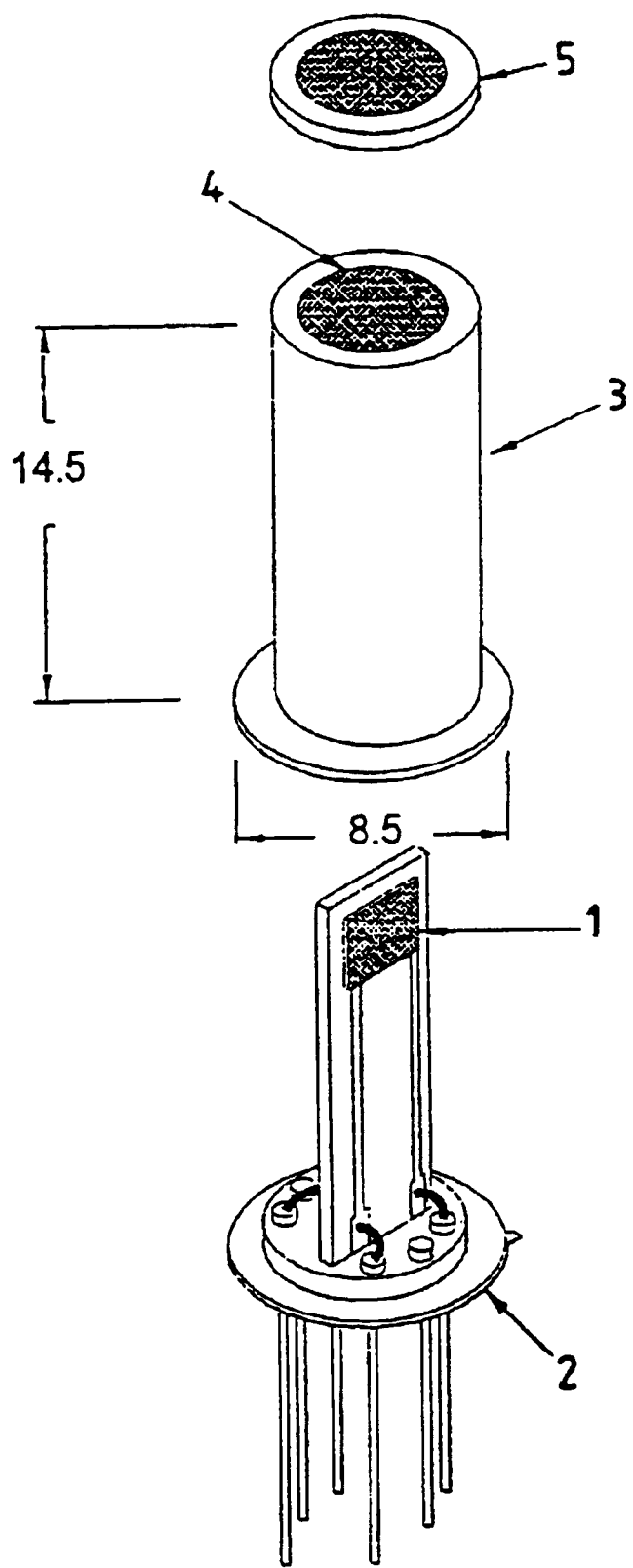
FIG. 1 illustrates a sensor according to one embodiment of the invention.
Figure 2:
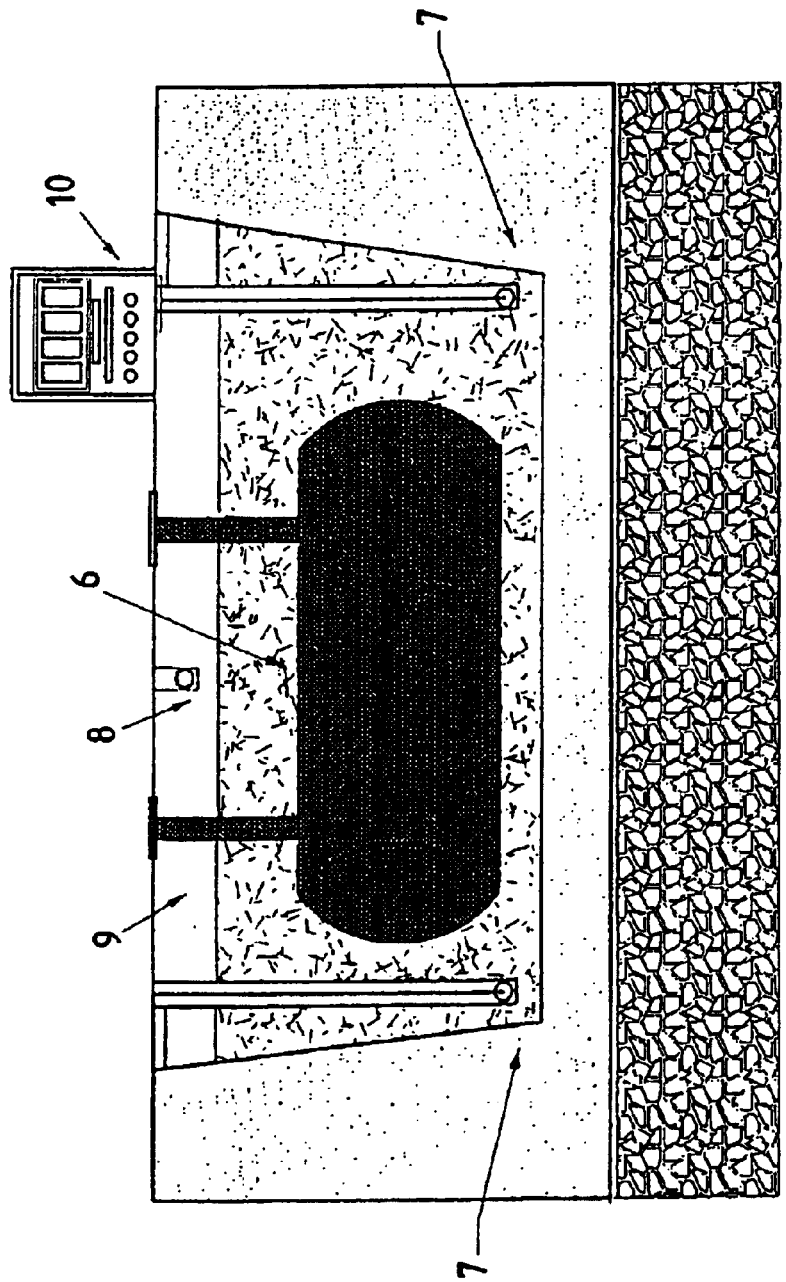
FIG. 2 illustrates an underground tank according to an embodiment of the invention.

FIG. 2 illustrates an underground tank 6 of a service station for leadless fuels with a configuration with three sensors for the embodiment of the present invention. Two sensors 7, like those described with a gas permeable membrane, are fixed in the ground at the sides of the tank, a sensor 8 without a membrane inserted in the chamber 9 above the tank. 10 illustrates the data acquisition switchboard.

Sensors such as those described above have a sensitivity which is such as to signal the presence of vapours of gasoline containing MTBE or MTBE alone with concentrations even less than 1 ppm in the air. The possibility of comparing the signals coming from the sensors fixed in the ground with those situated in the chamber above the tank over a period of time, make it possible to distinguish between leakages on the ground surface and losses from the underground tank.

In another embodiment of the same invention, sensors can be placed along an underground pipe around it and on the ground surface above. In this case the signals emitted from the sensors can be sent via radio to a central unit for collection and processing.

A few examples are provided below for a better understanding of the present invention but should not be considered as limiting the scope of the invention itself.

EXAMPLE 1

Using a sensor according to the one described above, and a tin container, conductivity measurements are carried out in the presence of gasoline vapours to which 10% of MTBE has been added.

Figure 3:
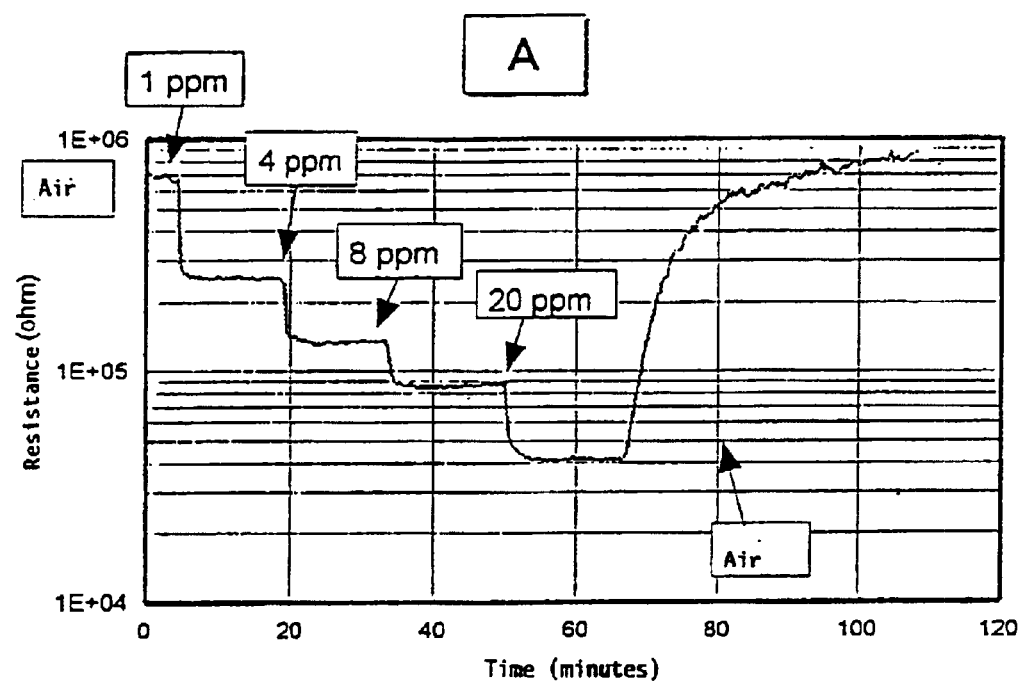
FIG. 3(a) illustrates the relationship between the kinetics response of a sensor according to one embodiment of the invention and time at various concentrations of gasoline.
FIG. 3(b) illustrates the relationship between the kinetics response of the sensor and the concentration of gasoline.
Figure 3:
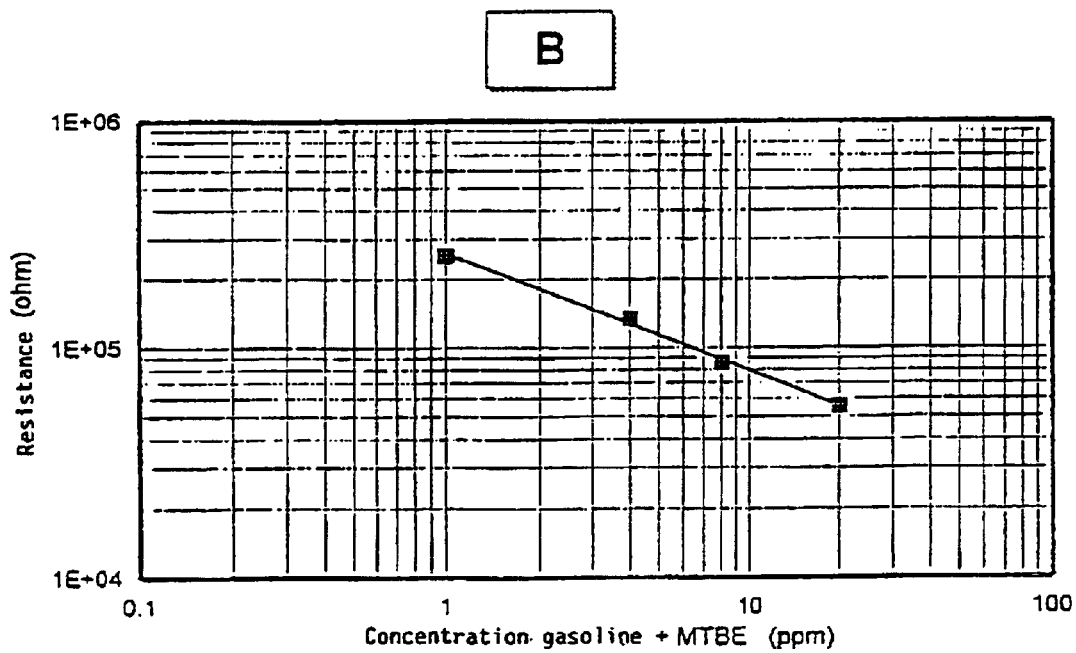

In FIG. 3.(a) the trace shows the kinetics response of the sensor in relation to the time at various concentrations of gasoline.

FIG. 3.(b) shows the variation in the resistance in relation to the concentrations of gasoline. As can be seen the response is proportional to the concentration logarithm and allows concentrations of less than 1 ppm to be detected.

EXAMPLE 2

With the procedure described above, a system consisting of two MTBE sensors and an electronic control unit is prepared.

One of the sensors, protected by an ePFTE membrane, is inserted, up to a depth of about 10 cm, in a tank of 50×40×30 cm full of sandy earth. The second sensor is placed at about 20 cm from the first and about 5 cm from the surface.

Figure 4:
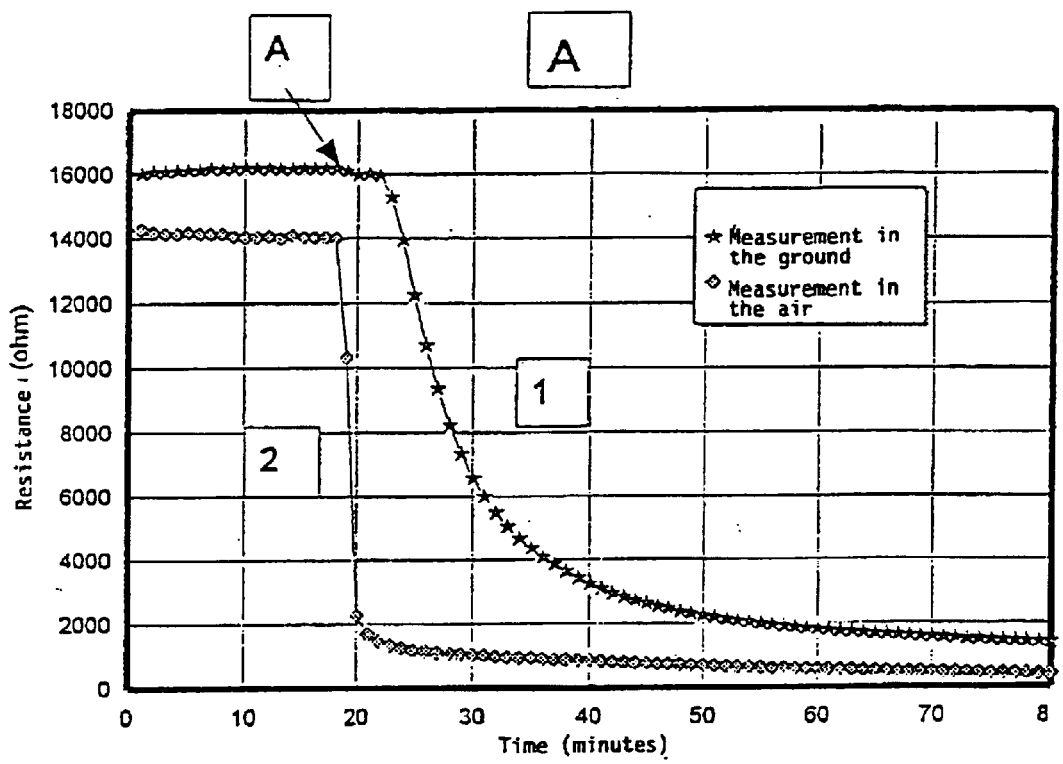
FIGS. 4(a) and 4(b) illustrate the kinetics response of a system including two MTBE sensors and electronic control unit according to an embodiment of the invention.
Figure 4:
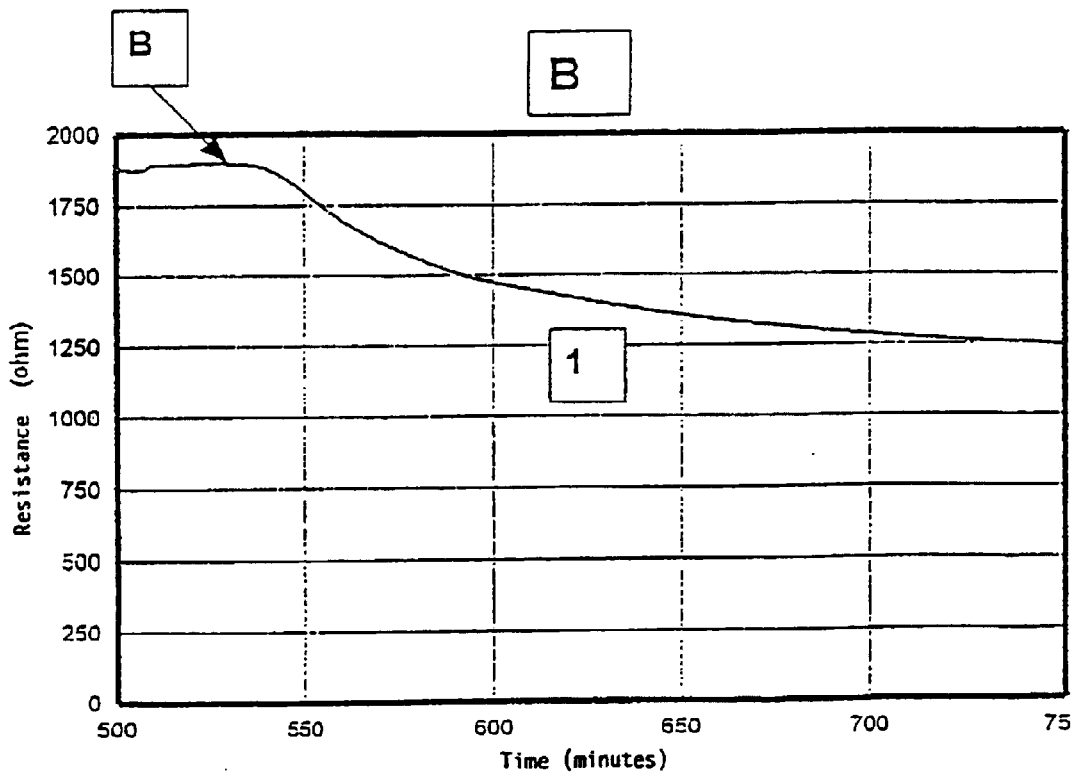

After a stabilization period of about 30 minutes 1 ml of gasoline containing 10% of MTBE is injected with a syringe into the ground, at a distance of 10 cm from the underground sensor and at a depth of 10 cm. In FIG. 4 the temporal point of the injection is indicated with the arrow A. As can be observed, the trace registered by the sensor in the air (2) indicates an almost immediate decrease in resistance, whereas the trace registered by the sensor in the ground (1) indicates a delay of about 5 min. before the decrease in resistance.

After a few hours, 1 ml of gasoline (indicated with the arrow B in FIG. 4B) is injected again. As can be observed, the trace of the sensor in the ground (1) begins to indicate a decrease in resistance starting from the level reached with the previous injection of gasoline. This shows that the sensor is capable of minitoring a further leakage also starting from ground which has already been polluted.

With respect to the trace in air, this starts from a much higher resistance value of the sensor as gasoline vapours dilute very rapidly in air, unlike the ground where the vapours interstitial tend to remain trapped.

The time delay of a few minutes in this case, shown by the response of the sensor fixed in the ground with respect to that in the air depends on the fact that in the earth interstitial vapours of gasoline and MTBE, although being mobile enough to allow this type of measurement, need a certain amount of time to spread from the leakage point to the sensor. In air the vapours obviously spread at a much faster rate and the sensor consequently does not show significant delays.

As mentioned in the description, the different behaviour of sensors in the ground and in the air enables a leakage in the surface to be distinguished from a leakage in depth in the ground.

What is claimed is:

1. A process for determining methyl ter butyl ether (MTBE) vapours, in concentrations equal to or higher than 0.1 ppm, in the ground and overlying atmosphere comprising:
   a) adopting a series of MTBE vapour sensors of which at least one in the earth, equipped with a membrane permeable to gases and impermeable to water, and at least one in the air on the surface of the ground, these sensors comprising
      a sensitive element made of a semi-conductor metal oxide containing platinum; and
      a heater capable of bringing the temperature of said sensitive element to a range of 300 and 500° C.;
   b) continuously observing the resistance variations of the sensitive elements by interaction with MTBE,
   comparing the signals emitted by the sensor in the earth and the sensor in the air on the ground-surface; and
   evaluating on the basis of this comparison the presence and concentration of MTBE in the surface layers or depths of the ground and in the atmosphere above the ground itself.

2. The process according to claim 1, wherein the sensitive element is produced with tin oxide.

3. A device for determining methyl ter butyl ether (MTBE) vapours comprising:
   a) a series of sensors of MTBE vapours each comprising a sensitive element produced with
      a 40 micron layer of semiconductor metal oxide containing 1% by weight of platinum,
      a heater capable of bringing the temperature of said sensitive element to a range of 300 to 500° C.,
   at least one of said sensors being equipped with a membrane permeable to gases and impermeable to water for the protection of said sensitive element;
   b) an electronic evaluation system configured to continuously record the variations in resistance of the sensitive elements by interaction with MTBE and further configured, to compare the signals emitted by the sensor in the air on the surface of the ground, and to evaluate on the basis of the compared signals the presence and concentration of MTBE in the surface layers or depths of the ground and in the atmosphere above the ground itself;
   wherein the semiconductor metal oxide is tin oxide.

* * * * *